United States Patent [19]

Winter et al.

[11] Patent Number: 4,586,828

[45] Date of Patent: May 6, 1986

[54] MEASURING DEVICE FOR DETECTING A LIQUID COMPONENT IN REFRIGERANT

[75] Inventors: Janos Winter, Mosevang; Jesper Lichtenberg, Alsgade, both of Denmark

[73] Assignee: Danfoss A/S, Nordborg, Denmark

[21] Appl. No.: 715,978

[22] Filed: Mar. 25, 1985

[30] Foreign Application Priority Data

Apr. 11, 1984 [DE] Fed. Rep. of Germany ....... 3413535

[51] Int. Cl.$^4$ .................. G01N 25/02; F25B 49/00
[52] U.S. Cl. ................................ 374/16; 62/126; 62/212; 374/15
[58] Field of Search ............ 374/16, 24, 25, 27, 374/110, 137, 145, 147; 62/125, 126; 374/5, 15, 164; 73/29; 62/212

[56] References Cited

U.S. PATENT DOCUMENTS

| | | | |
|---|---|---|---|
| 2,588,355 | 3/1952 | Burr et al. | 374/15 |
| 3,461,907 | 8/1969 | Wood | 137/386 |
| 3,577,743 | 5/1971 | Long | 62/212 |
| 3,587,244 | 6/1971 | Wood | 62/126 |
| 3,589,169 | 6/1971 | Lafitte et al. | 374/15 |
| 4,063,228 | 12/1973 | Egoenburger et al. | 73/29 |
| 4,249,697 | 2/1981 | Savage | 374/112 |
| 4,336,708 | 6/1982 | Hobgood et al. | 374/5 |
| 4,448,038 | 5/1984 | Barbier | 62/212 |

FOREIGN PATENT DOCUMENTS 0010761 1/1979 Japan ..................... 374/147

Primary Examiner—Charles Frankfort
Assistant Examiner—Thomas B. Will
Attorney, Agent, or Firm—Wayne B. Easton

[57] ABSTRACT

The invention relates to measuring apparatus for a refrigeration system for detecting a liquid component in refrigerant leaving the evaporator of the system through a suction conduit associated with a heating element heating the tube wall. The measuring apparatus includes a first temperature measuring sensor in thermal contact with the suction conduit located just sufficiently away from the heating element so as to be substantially unaffected by the heating element. A second temperature measuring reference sensor is in thermal contact with the suction conduit an optimum distance downstream from said heating element to provide a reference temperature indicative of the dry temperature of the refrigerant.

8 Claims, 4 Drawing Figures

MEASURING DEVICE FOR DETECTING A LIQUID COMPONENT IN REFRIGERANT

The invention relates to a measuring device for detecting a liquid component in refrigerant leaving the evaporator of a refrigerator or the like through a suction conduit associated with a heating element heating the tube wall, a temperature measuring sensor for giving a sensor signal and a reference value generator, wherein the difference between the sensor signal and reference value are evaluated.

In a known measuring device of this kind (DE-AS No. 10 55 018), the temperature measuring sensor is located in the immediate vicinity of the heating element, namely either circumferentially next to the heating element or radially outside the heating element. Having regard to the increasing coefficient of heat transfer between the tube wall and phase mixture as the proportion of unevaporated refrigerant in the phase mixture increases, one obtains at an unchanged heat output an equilibrium of heat flow through which the temperature of the temperature measuring sensor is to be influenced. The suction pressure in the suction conduit serves as the reference value. The difference is formed in a servo motor for the expansion valve upstream of the evaporator. When using a temperature sensor with a liquid/-vapour filling, the diaphragm or the piston of the servo motor is loaded on one side by the vapour pressure and on the other side by the pressure in the suction conduit. However, the measuring sensor temperature changes very little if dry instead of moist refrigerant flows through the suction conduit.

The invention is based on the problem of providing a measuring device of the aforementioned kind, in which the presence of liquid in the refrigerant can be detected with more certainty and the degree of moisture with more accuracy.

This problem is solved according to the invention in that the temperature measuring sensor is in thermal contact with the tube wall and is arranged at a spacing from the heating element along the tube.

The heat supplied by the heating element spreads in the tube wall, so that the temperature measuring sensor at a spacing upstream or downstream from from the heating element increases in temperature in relation to the unheated tube. If the refrigerant is dry, i.e. if it is present in vapour or gas form, there is a comparatively low coefficient of thermal transfer between tube wall and refrigerant. The measured temperature is correspondingly high. But if the refrigerant is moist, i.e. if it contains liquid, the coefficient of thermal transfer is higher and the temperature of the measuring sensor correspondingly lower. In the presence of liquid in the refrigerant, the sensor signal is therefore measurably less than when the refrigerant is dry. In this way one can, for example, regulate an expansion valve upstream of the evaporator in dependence on the degree of moisture, whether modulatingly or in the form of a two point control.

Simple experiments permit one to find the range of spacings in which there are marked differences in the measured temperature between refrigerant of predetermined moisture content and dry refrigerant. In the vicinity of the heating element, the temperature differences are still very small because different cooling could not yet take effect. When the spacing from the heating element becomes too large, the tube temperature in both cases approaches the suction gas temperature or a temperature primarily determined thereby, so that a sufficient temperature difference can again not be detected. Between these extremes, each refrigeration installation has an optimum spacing at which the difference between the measured temperatures for dry and moist refrigerant is the greatest.

In particular, the spacing between the heating element and temperature measuring sensor is 1 to 5 cm, preferably about 2 cm. Such a spacing is suitable for a large number of small and medium sized refrigeration plant.

In a preferred form of the invention, the reference value generator is formed by a reference value sensor disposed in thermal contact with the tube wall at a point having roughly the same temperature when there is liquid in the refrigerant as when the refrigerant is dry. Evaluation can then be conducted with the difference between the measured and reference temperatures, so that one obtains very accurate evaluation on the one hand and a very simple circuit on the other.

The reference temperature sensor can be at a much larger spacing from the heating element than the temperature measuring sensor. As already mentioned, over a wide spacing the tube wall temperatures with dry and moist refrigerant approximate to each other.

Desirably, the spacing between heating element and reference temperature sensor is 8 to 20 cm, preferably 10 to 15 cm.

Alternatively, the reference temperature sensor is spaced from the heating element a distance much less than is the temperature measuring sensor. About the same temperature also obtains in the region of the heating element irrespective of the condition of the refrigerant.

It is particularly favourable if the reference temperature sensor is circumferentially offset from the heating element. It is then at the same height as the heating element and substantially affected by the tube wall temperature as governed by the heating element.

Further, the sensors and heating element may be in a common housing. This simplifies installation.

It is also advantageous for the sensors and heating element to be thermally insulated from the outside. They will then not be influenced by changes in the surrounding temperature.

In an advantageous embodiment, the temperature measuring sensor and reference temperature sensor are thermoelectric elements with oppositely connected voltages. The series circuit of both sensors gives the differential signal offering the most favourable conditions for the evaluation.

Preferred examples of the invention will now be described with reference to the drawings, wherein.

Figure 1:
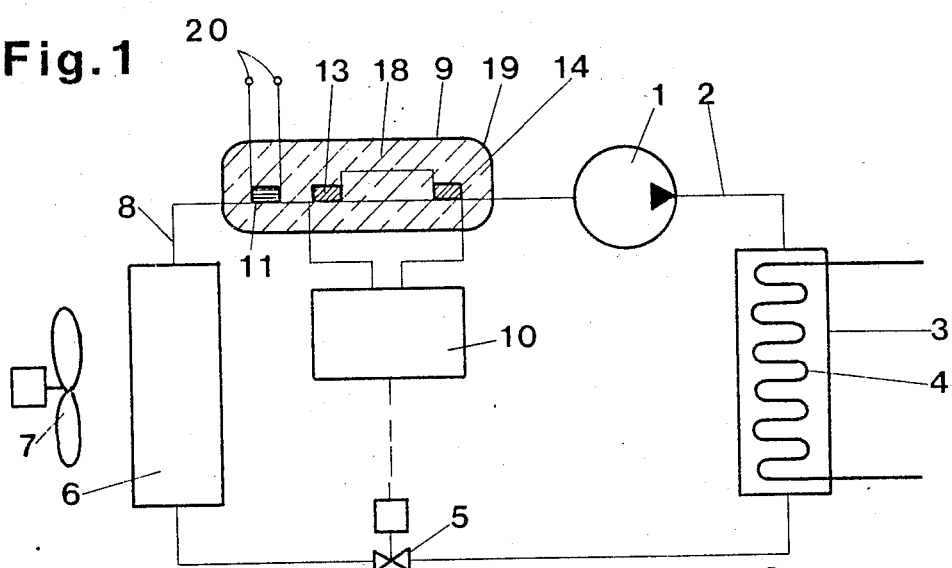
FIG. 1 is a diagrammatic representation of a heat pump installation with the measuring device of the invention.

In the heat pump installation of FIG. 1, a compressor 1 conveys gaseous refrigerant through a pressure conduit 2 into a condenser 3 in which water is heated in convolutions 4 of a secondary circuit. The thus liquified refrigerant arrives through an expansion valve 5 in an evaporator 6 which is cooled by a fan 7. Connected to the outlet of the evaporator there is a suction conduit 8 which leads to the compressor 1 again.

A measuring device 9 detects whether the suction conduit 8 contains dry refrigerant or whether the refrigerant still has liquid components and what degree of moisture. The measuring device 9 acts on a switching device 10 serving to control the expansion valve 5. As soon as the refrigerant flowing through the suction conduit 8 contains liquid, the expansion valve 5 will close until there is dry refrigerant again. The expansion valve 5 may also be controlled by the degree of moisture of the refrigerant.

The measuring device 9 has a heating element 11 lying against the tube wall 12 of suction conduit 8. The tube wall 12 is of a good thermally conducting material, especially a metal such as copper. A temperature measuring sensor 13 at a spacing $a_1$ from the heating element also lies against the tube wall 12. A reference temperature sensor 14 at a much larger spacing $a_2$ also lies against the tube wall 12. The heating element 11 is held on the suction conduit 8 by a clamping strap 15 and the sensors 13 and 14 by straps 16 and 17. These parts are surrounded by thermal insulation 18. The whole is contained in a housing 19. The terminals 20 of heating element 11 can be connected to a supply voltage determining the heat output.

Figure 3:
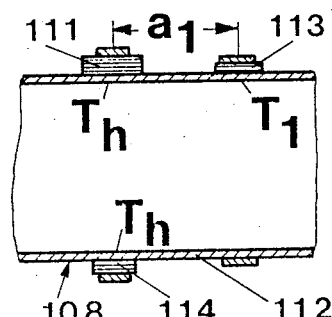
FIG. 3 shows a modification of the FIG. 2 measuring device.

In the modified embodiment of FIG. 3, whose corresponding parts have reference numerals increased by 100, the temperature measuring sensor 113 has the same spacing $a_1$ from the heating element 111. The reference sensor 114 on the other hand is in the same axial position as the heating element 111 and is only offset circumferentially.

Figure 4:
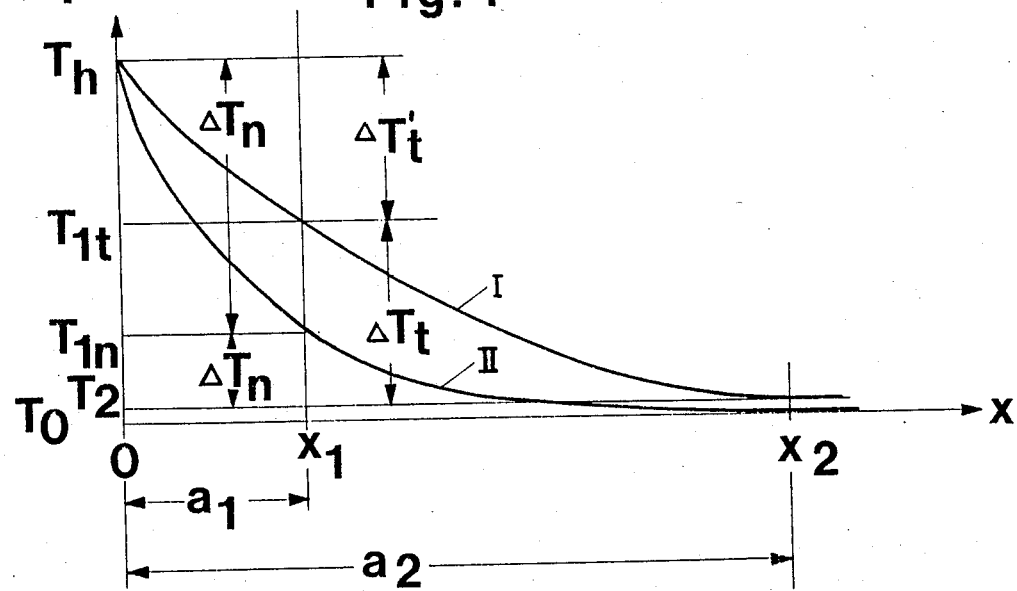
FIG. 4 is a graph of the temperature in the wall of the conduit.

The diagram of FIG. 4 shows the temperature T of tube wall 12 plotted against the length x of tube 8. It is assumed that the heating element 11 is at the position x=0 and brings the tube wall to a temperature $T_h$. The x-axis corresponds to a base temperature $T_o$ predetermined by the suction pressure of the refrigerant and the surrounding temperature. Curve I shows the temperature course in tube wall 12 when the refrigerant is dry, i.e. contains no liquid. Curve II shows the temperature course when the refrigerant is wet and there is therefore a larger coefficient of heat transfer between tube wall and refrigerant. The two curves start at the same temperature $T_h$ and approach the base temperature $T_o$ as x increases. The temperature measuring sensor 13 disposed at position $x_1$ from the heating element 11 therefore measures the temperature $T_{1t}$ with dry refrigerant and $T_{1n}$ with a wet refrigerant. The reference temperature sensor 14 arranged at the position $x_2$ in both cases measures a value $T_2$ slightly above the base temperature $T_o$. Curves for various degrees of moisture run between curves I and II.

The two curves I and II are exponential curves having the course $$f(x) = (T_h - T_o) \cdot e^{-mx} \text{ with } m = \sqrt{\frac{a \times U}{1 \times A}}$$

wherein
$T_h$ = the temperature of tube wall 12 in the region of heating element 11
$T_o$ = the suction gas temperature
$a$ = the coefficient of heat transfer between tube wall and refrigerant $1$ = the thermal transmission along tube wall 12
$U$ = the external circumference of tube 12
$A$ = the cross-sectional area of tube 12.

Figure 2:
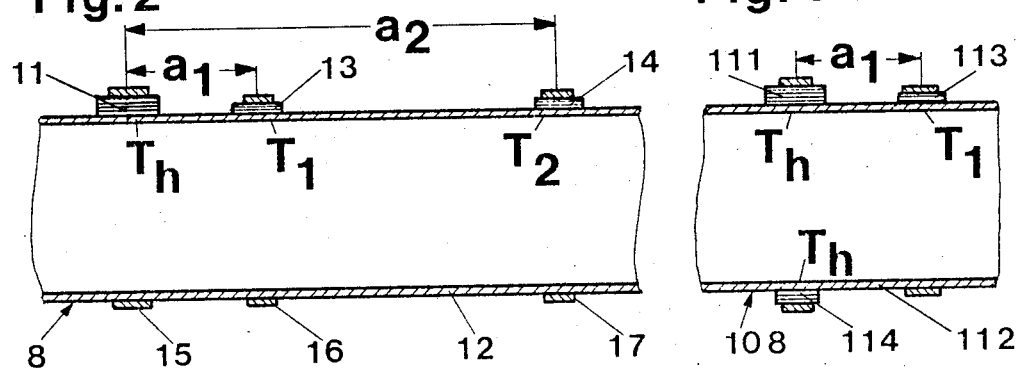
FIG. 2 shows the FIG. 1 measuring device to an enlarged scale.

In the FIGS. 1 and 2 embodiment, the temperature sensors 13 and 14 are thermoelements with oppositely connected voltages, so that the switching apparatus 10 is supplied with the voltage difference corresponding to the temperature difference $\Delta T_t$ with dry refrigerant and the much smaller temperature difference $\Delta T_n$ with wet refrigerant. Such differences can be evaluated by the switching apparatus 10 without effort and control the expansion valve 5 accordingly.

In the FIG. 3 embodiment, use is made of the temperature $T_h$ in the region of the heating element 11 instead of the low reference temperature $T_2$. In this case, the temperature difference $\Delta T'_t$ is available to the switching apparatus 10 with dry refrigerant and $\Delta T'_n$ with wet refrigerant. These differences can likewise be easily evaluated.

Normal resistance heating elements can be used as the heating element. In some cases PTC resistors are advisable. The heat output can be relatively low. It must merely have a value so that a clear difference between the two curves I and II occurs at the given spacing $a_1$.

The temperature sensors may have any desired known construction and are particularly in the form of a temperature-dependent resistor or thermoelement. Instead of the base temperature of the tube wall, one can use the suction gas temperature or the associated suction gas pressure as the reference value.

As a practical value for the spacing $a_1$ it is recommended to use about 2 cm and for the larger spacing $a_2$ about 10 to 15 cm. These values are typical for tube sizes with an external diameter of 17 to 25 mm and an internal diameter of 15 to 23 mm. For the coefficient of thermal transfer $a$, typical values are 200 J/m$^2$·s·°C. for the dry condition and about 2000 J/m$^2$·s·°C. for the wet condition of the refrigerant. This corresponds to a factor of 10. Although this factor decreases somewhat with very high flow speeds, it suffices for clearly differentiating the phase condition of the refrigerant.

We claim:
1. Measuring appratus for a refrigeration system of the type having in series a compressor, a condenser, an expansion valve, an evaporator and a suction conduit between said evaporator and said compressor having an associated heating element for heating said suction conduit, said apparatus including means for detecting the relative quantity of a liquid component in refrigerant in said suction conduit leaving said evaporator, said means including a first temperature measuring sensor in thermal contact with said suction conduit providing a first sensor output signal, said first temperature measuring sensor being located just sufficiently away from said heating element so as to be substantially unaffected by said heating element, and a second temperature measuring sensor in thermal contact with said suction conduit to provide a reference temperature output signal, said second temperature measuring sensor being located at a point where the temperature of said suction conduit is substantially unaffected by the relative quantity of said liquid component in said refrigerant, whereby the difference between the first sensor output signal and the reference temperature output signal is indicative of the relative quantity of said liquid component in said refrigerant.

2. Measuring apparatus according to claim 1 characterized in that said first sensor is spaced from said heating element a distance on the order of 2 cm.

3. Measuring apparatus according to claim 1 characterized in that said second sensor is in thermal contact with said suction conduit at a point having approximately the same temperature when said refrigerant contains a liquid component as when said refrigerant is dry.

4. Measuring apparatus according to claim 2 characterized in that the spacing between said heating element and said second sensor is on the order of 10 to 15 cm.

5. Measuring apparatus according to claim 1 characterized in that said second temperature sensor is circumferentially offset from said heating element.

6. Measuring apparatus according to claim 1 characterized in that said sensors and heating elements are thermally insulated from the outside.

7. Measuring apparatus according to claim 1 characterized in that said sensors are thermo-electric elements with oppositely connected voltages.

8. Measuring apparatus for a refrigeration system according to claim 1 wherein said second sensor is positioned an optimum downstream from said heating element.

* * * * *